US006939361B1

(12) United States Patent
Kleshinski (10) Patent No.: US 6,939,361 B1
(45) Date of Patent: Sep. 6, 2005

(54) GUIDEWIRE FOR A FREE STANDING INTERVASCULAR DEVICE HAVING AN INTEGRAL STOP MECHANISM

(75) Inventor: Stephen J. Kleshinski, Scituate, MA (US)

(73) Assignee: NMT Medical, Inc., Boston, MA (US)

( * ) Notice: Subject to any disclaimer, the term of this patent is extended or adjusted under 35 U.S.C. 154(b) by 611 days.

(21) Appl. No.: 09/666,452

(22) Filed: Sep. 21, 2000

Related U.S. Application Data (60) Provisional application No. 60/155,090, filed on Sep. 22, 1999.

(51) Int. Cl.[7] ............................................ A61M 29/00
(52) U.S. Cl. ...................................... 606/200; 600/434
(58) Field of Search ................................ 606/200, 113, 606/114, 127; 623/1.11; 604/104; 600/127, 434, 585

(56) References Cited

U.S. PATENT DOCUMENTS

| 3,874,388 A | 4/1975 | King et al. ............. 128/334 R |
| 4,007,743 A | 2/1977 | Blake ..................... 128/334 R |
| 4,425,908 A | 1/1984 | Simon ......................... 128/1 R |
| 4,817,600 A | 4/1989 | Herms et al. ........... 128/303 R |
| 4,836,204 A | 6/1989 | Landymore et al. .... 128/334 R |
| 4,921,484 A | 5/1990 | Hillstead .................... 604/104 |
| 4,985,014 A | 1/1991 | Orejola ........................ 600/16 |
| 5,030,199 A | 7/1991 | Barwick et al. ............. 600/29 |
| 5,041,129 A | 8/1991 | Hayhurst et al. ........... 606/232 |
| 5,042,976 A | 8/1991 | Ishitsu et al. ................ 604/96 |
| 5,057,114 A | 10/1991 | Wittich et al. .............. 606/127 |
| 5,073,166 A | 12/1991 | Parks et al. ................... 609/93 |
| 5,108,418 A | 4/1992 | Lefebvre .................... 606/200 |
| 5,108,420 A | 4/1992 | Marks ........................ 606/213 |
| 5,112,310 A | 5/1992 | Grobe ........................ 604/175 |
| 5,133,733 A | 7/1992 | Rasmussen et al. ........ 606/200 |
| 5,176,687 A | 1/1993 | Hasson et al. .............. 606/114 |
| 5,190,528 A | 3/1993 | Fonger et al. .............. 604/171 |
| 5,192,301 A | 3/1993 | Kamiya et al. ............. 606/213 |
| 5,242,462 A | 9/1993 | El-Nounou et al. ......... 606/200 |

(Continued)

FOREIGN PATENT DOCUMENTS

| WO | WO98/38920 | 9/1998 |
| WO | WO98/39046 | 9/1998 |
| WO | WO98/39053 | 9/1998 |
| WO | WO 03/077733 A2 | 9/2003 |

OTHER PUBLICATIONS

"Trans–septal Catheterization for Radiofrequency Catheter Ablation of Cardiac Arrhythmias. Results and Safety of a Simplified Method," by R. DePonti, et al., European Heart Journal, vol. 19, Jun. 1998, pp. 943–950.

"The Puncture Needle as Guidewire: Needle Guide Technique for Percutaneous Nephrostomy," by Irvin F. Hawkins, Jr., M.D., et al., Seminars in Interventional Radiology, vol. 4, No. 2, Jun. 1987, pp. 126–130.

"PFO and Stroke: The Hidden Connection," by Paul Kramer, MD, Endovascular Today, http://www.endovasculartoday.com/02_current/10.html, printed Oct. 9, 2003.

(Continued)

*Primary Examiner*—Kevin T. Truong
(74) *Attorney, Agent, or Firm*—Testa, Hurwitz & Thibeault, LLP (57) ABSTRACT

An elongate guidewire for use with a free, unsecured, intervascular device having an elongate, enclosed, open ended channel for receiving the guidewire. The guidewire includes an elongate, flexible body having an outer dimension which is less than the inner dimension of the channel and an expandable and contractable stop member mounted on the guidewire body for movement between a first contracted position and a second expanded position. The expandable and contractable stop member is dimensioned in the first contracted position to move through said channel and in the second expanded position to preclude movement of said stop member through the channel.

47 Claims, 4 Drawing Sheets

U.S. PATENT DOCUMENTS

| | | | |
|---|---|---|---|
| 5,284,488 A | 2/1994 | Sideris | 606/213 |
| 5,312,341 A | 5/1994 | Turi | 604/96 |
| 5,312,417 A | 5/1994 | Wilk | 606/114 |
| 5,357,979 A | 10/1994 | Imran | 128/772 |
| 5,370,647 A | 12/1994 | Graber et al. | 606/127 |
| 5,370,657 A | 12/1994 | Irie | 606/200 |
| 5,370,661 A | 12/1994 | Branch | 606/232 |
| 5,403,338 A | 4/1995 | Milo | 606/184 |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,464,408 A | 11/1995 | Duc | 606/108 |
| 5,507,811 A | 4/1996 | Koike et al. | 623/11 |
| 5,540,712 A | 7/1996 | Kleshinski et al. | 606/198 |
| 5,545,138 A | 8/1996 | Fugoso et al. | 604/102 |
| 5,577,299 A | 11/1996 | Thompson et al. | 24/131 C |
| 5,578,045 A | 11/1996 | Das | 606/151 |
| 5,601,595 A | 2/1997 | Smith | 606/200 |
| 5,634,936 A | 6/1997 | Linden et al. | 606/213 |
| 5,653,684 A | 8/1997 | Laptewicz et al. | 604/22 |
| 5,667,525 A | 9/1997 | Ishibashi | 606/206 |
| 5,669,933 A | 9/1997 | Simon et al. | 600/200 |
| 5,683,411 A | 11/1997 | Kavteladze et al. | 606/200 |
| 5,702,421 A | 12/1997 | Schneidt | 606/213 |
| 5,709,707 A | 1/1998 | Lock et al. | 606/213 |
| 5,720,754 A | 2/1998 | Middleman et al. | 606/127 |
| 5,725,552 A | 3/1998 | Kotula et al. | 606/213 |
| 5,733,294 A | 3/1998 | Forber et al. | 606/151 |
| 5,741,297 A | 4/1998 | Simon | 606/213 |
| 5,746,765 A | 5/1998 | Kleshinski et al. | 606/198 |
| 5,776,162 A | 7/1998 | Kleshinski | 606/198 |
| 5,800,457 A | 9/1998 | Gelbfish | 606/200 |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,836,968 A | 11/1998 | Simon et al. | 606/200 |
| 5,846,260 A | 12/1998 | Maahs | |
| 5,853,420 A | 12/1998 | Chevillon et al. | 606/200 |
| 5,868,753 A | 2/1999 | Schatz | 606/108 |
| 5,876,367 A | 3/1999 | Kaganov et al. | |
| 5,879,366 A | 3/1999 | Shaw et al. | 606/213 |
| 5,895,404 A | 4/1999 | Ruiz | 606/185 |
| 5,902,317 A | 5/1999 | Kleshinski et al. | 606/198 |
| 5,904,703 A | 5/1999 | Gilson | 606/213 |
| 5,919,200 A | 7/1999 | Stambaugh et al. | 606/159 |
| 5,944,738 A | 8/1999 | Amplatz et al. | 606/213 |
| 5,976,172 A | 11/1999 | Homsma et al. | 606/200 |
| 5,976,174 A | 11/1999 | Ruiz | 606/213 |
| 5,997,556 A | 12/1999 | Tanner | 606/153 |
| 6,007,558 A | 12/1999 | Ravenscroft et al. | 606/200 |
| 6,024,756 A | 2/2000 | Huebsch et al. | 606/213 |
| 6,030,007 A | 2/2000 | Bassily et al. | 289/1.5 |
| 6,030,405 A | 2/2000 | Zarbatany et al. | 606/191 |
| 6,056,760 A | 5/2000 | Koike et al. | 606/148 |
| 6,066,158 A | 5/2000 | Engelson et al. | 606/200 |
| 6,080,182 A | 6/2000 | Shaw et al. | 606/213 |
| 6,086,610 A | 7/2000 | Duerig et al. | 623/1 |
| 6,096,053 A | 8/2000 | Bates | 606/159 |
| 6,106,532 A | 8/2000 | Koike et al. | 606/138 |
| 6,117,159 A | 9/2000 | Huebsch et al. | 606/213 |
| 6,129,755 A | 10/2000 | Mathis et al. | 623/1.15 |
| 6,149,664 A | 11/2000 | Kurz | 606/194 |
| 6,156,055 A | 12/2000 | Ravenscroft | 606/206 |
| 6,168,579 B1 | 1/2001 | Tsugita | 604/96.01 |
| 6,171,329 B1 | 1/2001 | Shaw et al. | 606/213 |
| 6,174,322 B1 | 1/2001 | Schneidt | 606/213 |
| 6,179,859 B1 | 1/2001 | Bates et al. | 606/200 |
| 6,203,559 B1 | 3/2001 | Davis et al. | 606/198 |
| 6,206,907 B1 | 3/2001 | Marino et al. | 606/215 |
| 6,213,976 B1 | 4/2001 | Trerotola | 604/104 |
| 6,214,029 B1 | 4/2001 | Thill et al. | 606/213 |
| 6,216,696 B1 | 4/2001 | Van den Berg | 128/207.14 |
| 6,221,006 B1 | 4/2001 | Dubrul et al. | 600/159 |
| 6,221,092 B1 | 4/2001 | Koike et al. | 606/213 |
| 6,245,012 B1 | 6/2001 | Kleshinski | 600/200 |
| 6,258,026 B1 | 7/2001 | Ravenscroft et al. | 600/200 |
| 6,290,674 B1 | 9/2001 | Roue et al. | 604/107 |
| 6,312,446 B1 | 11/2001 | Huebsch et al. | 606/213 |
| 6,336,934 B1 * | 1/2002 | Gilson et al. | 606/200 |
| 6,342,064 B1 | 1/2002 | Koike et al. | 606/213 |
| 6,346,074 B1 | 2/2002 | Roth | 600/121 |
| 6,352,531 B1 | 3/2002 | O'Connor et al. | 606/15 |
| 6,355,052 B1 | 3/2002 | Neuss et al. | 606/213 |
| 6,371,971 B1 * | 4/2002 | Tsugita et al. | 606/200 |
| 6,375,671 B1 | 4/2002 | Kobayashi et al. | 606/213 |
| 6,379,368 B1 | 4/2002 | Corcoran et al. | 606/153 |
| 6,440,152 B1 | 8/2002 | Gainor et al. | 606/213 |
| 6,482,210 B1 | 11/2002 | Skiba et al. | 606/86 |
| 6,537,198 B1 | 3/2003 | Vidlund et al. | 600/16 |
| 6,623,518 B2 | 9/2003 | Thompson et al. | |
| 2001/0037129 A1 | 11/2001 | Thill | 606/213 |
| 2002/0099389 A1 | 7/2002 | Michler et al. | 606/139 |
| 2002/0120323 A1 | 8/2002 | Thompson et al. | |
| 2002/0128680 A1 | 9/2002 | Pavlovic | 606/200 |
| 2002/0183786 A1 | 12/2002 | Girton | 606/213 |
| 2002/0183787 A1 | 12/2002 | Wahr et al. | 606/213 |
| 2003/0045893 A1 | 3/2003 | Ginn | 606/151 |
| 2003/0050665 A1 | 3/2003 | Ginn | 606/215 |
| 2003/0208232 A1 | 11/2003 | Blaeser et al. | |

OTHER PUBLICATIONS

"The Puncture Technique: A New Method of Transcatheter Closure of Patent Foramen Ovale," by Carlos E. Ruiz, M.D., Ph.D., et al., Catheterization and Cardiovascular Interventions, vol. 53, 2001, pp. 369–372.

"New Transseptal Puncture Technique for Transcatheter Closure of Patent Foramen Ovale," by Robert J. Sommer, M.D., et al., Mount Sinai Medical Center, New York, New York, publication date unknown but believed to be Jun. 2002 or earlier.

"Elastic Deployment," SMST–2000 Proceedings of the International Conference on Shape Memory and Superelastic Technologies, Apr. 30 to May 4, 2000, Asilomar Conference Center, 3 pages.

"Microvena—Uniquely Innovative Interventional Products," Microvena press release from http://www.microvena.com/MVC–NEWS.html, printed on Jan. 27, 2003.

James Hansen, "Metals that Remember," Science 81, Jun., pp. 44–47.

Morris Simon and Aubrey M. Palestrant "Transvenous Devices for the Management of Pulmonary Embolism", Cardiovascular and Interventional Radiology by Springer–Verlag, 308–318, 1980.

Morris Simon, M.D., Roy Kaplow, Ph.D., Edwin Salzman, M.D., and David Freiman, M.D., A Vena Cava Filter Using Thermal Shape Memory Alloy, Radiology, vol. 125, No. 1, Oct. 1977, pp. 89–94.

* cited by examiner

GUIDEWIRE FOR A FREE STANDING INTERVASCULAR DEVICE HAVING AN INTEGRAL STOP MECHANISM

This application claims the benefit of U.S. Provisional Patent Application Ser. No. 60/155,090 filed on Sep. 22, 1999.

TECHNICAL FIELD

The present invention relates generally to a guidewire for positioning and removing emboli capture and recovery devices (ECRD) such as small filters in a vein or artery, and more particularly to a guidewire with an integral stop mechanism which, when expanded or extended, permits the guide wire to move freely with respect to the filter while preventing the guidewire from being inadvertently removed from association with the filter and when collapsed or retracted permits the guidewire to be inserted through or removed from the filter.

BACKGROUND OF THE INVENTION

In recent years, a number of intervascular medical devices have been designed which are adapted for compression into a small size to facilitate introduction into a body vessel such as an arterial or vascular passageway and which are subsequently expandable into contact with walls of the passageway. These devices, among others, include stents, such as those shown by U.S. Pat. No. 5,540,712 and blood clot filters such as those shown by U.S. Pat. No. 5,669,933 which expand and are held in position by engagement with the inner wall of a vessel. It has been found to be advantageous to form such devices of a thermal shape memory material having a first, relatively pliable low temperature condition and a second, relatively rigid high-temperature condition. By forming such devices of temperature responsive material, the device in a flexible and reduced stress state may be compressed to fit within the bore of a delivery catheter when exposed to a temperature below a predetermined transition temperature, but at temperatures at or above the transition temperature, the device expands and becomes relatively rigid.

Known self expanding medical devices have been formed of Nitinol, an alloy of titanium and nickel which provides the device with a thermal memory. The unique characteristic of this alloy is its thermally triggered shape memory, which allows a device constructed of the alloy to be cooled below a temperature transformation level to a martensitic state and thereby softened for loading into a catheter in a relatively compressed and elongated state, and to regain the memorized shape in an austenitic state when warmed to a selected temperature, above the temperature transformation level, such as human body temperature. The two interchangeable shapes are possible because is of the two distinct microcrystalline structures that are interchangeable with a small variation in temperature. The temperature at which the device assumes its first configuration may be varied within wide limits by changing the composition of the alloy. Thus, while for human use the alloy may be focused on a transition temperature range close to 98.6° F., the alloy readily may be modified for use in animals with different body temperatures.

In recent years advances have been made in the treatment of blood vessel stenosis or occlusion by plaque, thrombi, embolic, or other deposits which adversely reduce or block the flow of blood through a vessel. Balloon angioplasty or similar transluminal treatments have become common for some blood vessel lesions, but for all such procedures, plaque and emboli dislodged during the procedure are free to flow within the lumen of the vessel and possibly cause substantial injury to a patient.

In an attempt to contain and remove emboli and other debris, balloon angioplasty coupled with irrigation and aspiration has been performed as illustrated by U.S. Pat. No. 5,883,644 and International Publication No. WO 98/39046 to Zadno-Azizi et al. This procedure requires complete vessel occlusion cutting off all blood flow which imposes severe time constraints on the procedure. Additionally, the balloons involved in the procedure are affixed to elongate guidewires or small elongate catheters which extend for a substantial distance through blood vessels to the location of the stenosis or occlusion, and it is practically impossible to prevent some back and forth longitudinal motion of these elongate elements within a vessel during a procedure. This movement of the guidewire or catheter to which a balloon is attached causes the balloon to move back and forth and abrade emboli from the vessel wall downstream of the balloon containment area.

Angioplasty is often not a preferred treatment for lesions in the carotid artery because dislodged plaque can enter arterial vessels of the brain causing brain damage or even death. As indicated by U.S. Pat. No. 5,879,367 to Kaganov et al., carotid endarterectomy is a surgical procedure used to remove a lesion in the carotid artery, but this procedure also involves substantial risk of dislodged embolic material.

In an attempt to contain dislodged emboli during a procedure to clear blood vessel stenosis or occlusion, a variety of distal filters have been devised such as those shown by U.S. Pat. No. 5,814,064 and International Publication Nos. WO 98/38920 and WO 98/39053 to Daniel et al. as well as U.S. Pat. No. 5,827,324 to Cassell et al., 5,846,260 to Maahs and 5,876,367 to Kaganov et al. These filters are secured to the distal portion of a guidewire or catheter and are deployed distally from the stenosis or occlusion to capture embolic material. Once the distal filter is positioned and expanded into contact with the wall of the blood vessel, an angioplasty balloon, a stent, or other devices are introduced over the proximal end of the guidewire or catheter to which the filter is attached and moved into position in the area of the occlusion or stenosis spaced proximally from the filter.

Known guidewire or catheter attached distal filters have been subject to a number of disadvantages. First, since the elongate catheter or guidewire to which the filter is attached is used to guide over the wire devices during a subsequent procedure, it is extremely difficult if not impossible to prevent longitudinal movement of the wire or catheter after the filter has been deployed. This causes the filter to move back and forth within the vessel with resultant abrasion by the filter of the vessel wall, and such abrasion not only causes trauma to the vessel wall but also operates to dislodge debris which is free to flow distally of the filter. Thus filter movement after the filter is deployed somewhat defeats the purpose of the filter. Also, it is often desirable during a procedure to exchange guidewires, and such an exchange is not possible with an attached filter.

Additionally, the retrieval of known distal filters while retaining captured embolic material has proven to be problematic. Many cone shaped filters with wide, upstream proximal open ends tend to eject captured embolic material through the open end as the filter is collapsed. Also, many distal filters are formed by a mesh material which is expanded by a filter frame, and when the frame closes to collapse the filter for withdrawal through a catheter, the mesh folds creating outwardly projecting pleats. These pleats snag on the withdrawal of the catheter making retrieval of the filter difficult and often causing the filter to spill captured embolic material.

Recently, it has become of concern that if the guidewire is made to be displaceable with respect to a filter or other intervascular device, there is the possibility that the device could become disassociated with the guidewire and consequently could migrate and become lost within the vessel. Accordingly, there is a need for a mechanism to provide selective association of the guidewire with a free standing, unsecured intervascular device when necessary while also being capable of stopping travel of the device away from the stenosis or occlusion in order to alleviate concerns regarding free migration of the device within a blood vessel.

SUMMARY OF THE INVENTION

A primary object of the present invention is to provide a combination intervascular device and guidewire wherein the guidewire is longitudinally movable relative to the intervascular device.

It is an object of the present invention to provide a novel and improved guidewire for confidently positioning a free standing filter for expansion within a blood vessel to capture dislodged embolic material.

Another object of the present invention is to provide a novel and improved guidewire for confidently positioning a free standing filter for use during a procedure to treat blood vessel stenosis or occlusion which does not cause filter movement which results in trauma to the luminal wall during guidewire, balloon and stent exchanges and which can be associated with the filter in a manner to facilitate longitudinal movement of the guidewire relative to the filter while precluding filter migration.

A further object of the present invention is to provide a novel and improved guidewire for positioning a free standing filter for use during a procedure to treat blood vessel stenosis or occlusion which is formed to facilitate intraprocedural guidewire exchanges and which reduces concern for the disassociation of the filter from the guidewire during normal procedures.

Yet another object of the present invention is to provide a novel and improved guidewire for use with a free standing filter during a procedure to treat blood vessel stenosis or occlusion which is formed to remain stationary after expansion independent of guidewire or catheter motion which maintains an association with the filter to ensure proper removal of the filter upon completion of the procedure.

A still further object of the present invention is to provide a novel and improved guidewire for association with the positioning of ECRD including a stop mechanism in the area of a distal end thereof to expand or extend and collapse or retract on actuation thereby forming a mechanical stop preventing the guidewire from being inadvertently removed from the ECRD.

These and other objects of the present invention are accomplished by providing an elongated guidewire having a stop mechanism thereon which is receivable in a receiving member extending centrally through an intervascular device provided with an open ended channel which may be configured to receive a plurality of different sized guidewires. The guidewire stop mechanism is positioned in the area of a distal end of the guidewire and may be selectively expanded or extended and collapsed or retracted to permit selective association with the intervascular device. When positioned through the receiving member of the intervascular device, the stop mechanism can be expanded or extended to prevent the loss of the device while still permitting the guidewire to move longitudinally with respect to the device. The stop mechanism may take on numerous configurations namely that of a balloon, a grappling hook, a buckled tube, a braided structure, barbs, biased bosses or any mechanism which is remotely expandable or extendable and collapsible or retractable from a guidewire. In the retracted position, the stop member should pass freely through the receiving member of the intervascular device, but in the expanded position, the stop member should be radially spaced from the inner wall of a blood vessel while precluding migration of the intervascular device over the distal end of the guidewire.

DESCRIPTION OF THE PREFERRED EMBODIMENTS

Figure 1:
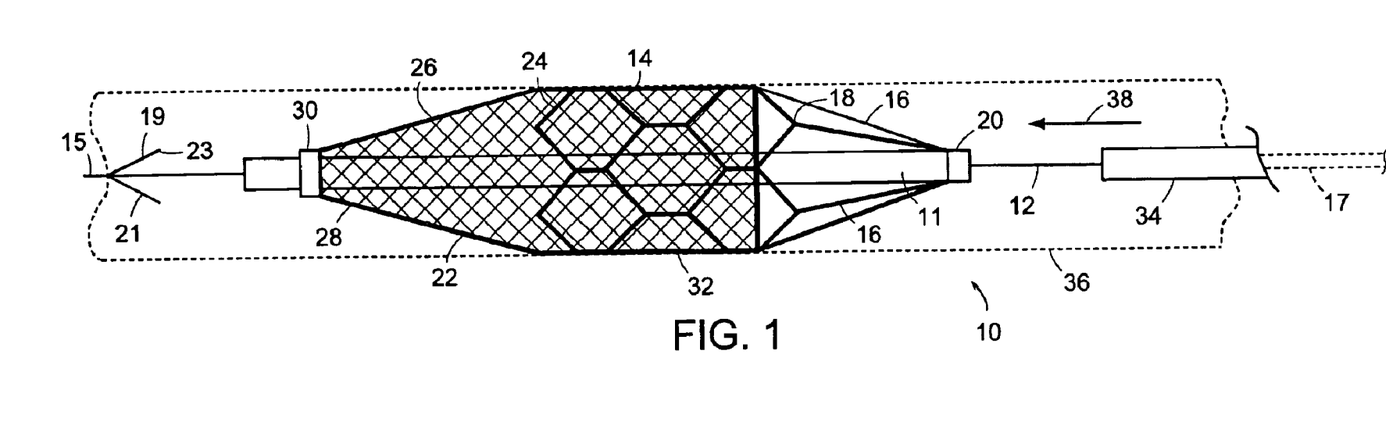
FIG. 1 is a view in side elevation of the free standing filter which can readily accommodate the guidewire of the present invention in the expanded configuration having the guidewire in accordance with the present invention positioned therein with the stop member expanded.

Referring to FIG. 1, a free standing filter 10 which is suitable for accommodating the guidewire 12 in accordance with the present invention is formed around a central tube 11 defining an open ended channel which forms the longitudinal axis for the filter 10 and which slidingly receives the guidewire 12. The frame of the filter is formed by a stent 14 which may be collapsed inwardly toward the tube 11 and which expands outwardly away from the tube to the substantially cylindrical open ended configuration shown in the drawings. Ideally, this stent is formed of thermal shape memory material and is of the type shown by U.S. Pat. No. 5,540,712, although other expandable stents can be used. The stent 14 is coupled at one end to the central tube 11 by elongate lead wires 16 which extend between an open proximal end 18 of the stent and a spaced coupling 20 which is secured to the central tube 11. It should be readily appreciated by those skilled in the art that the guidewire 12 in accordance with present invention may be used in conjunction with any ECRD, stent, or other intervascular medical device sized for positioning in a body vessel such as an arterial or vascular passageway without departing from the spirit and scope of the present invention.

In the example illustrated in FIG. 1, extending around the stent 14 and attached thereto is a flexible, fine mesh filter material 22 which opens at the proximal end 18 of the stent and covers the body of the stent. Ideally, the stent extends over this mesh filter material. At the distal end 24 of the stent, the fine mesh filter material projects outwardly to form a flexible conical section 26 with an apex 28 connected to a coupling 30 which slides on the tube 11 in spaced relation to the stent distal end 24. Thus when the stent expands as shown in the drawings, the mesh filter material forms a substantially cylindrical section 32 which opens at the proximal end of the stent and a flexible, closed conical section 26 which extends beyond the distal end of the stent to catch and collect small particles. The fine filter mesh may be formed of suitable biocompatible material such as polyester or a PTFE material and is coated with thromboresistant materials such as, for example, Phosphoral Choline or Hyaluronic Acid. The mesh is a braided material or elastomeric mesh which normally conforms to the exterior shape of the central tube 11, but which stretches to expand outwardly away from the tube when the stent 24 expands. Thus the mesh is biased toward the tube 11, and when the stent collapses inwardly toward the tube, the mesh contracts back to the exterior shape of the tube and does not form pleats.

In the operation of the filter 10, the stent with the mesh filter material is inserted in a collapsed condition into a delivery tube 34 and guidewire 12 extends through the central tube 11. Then the delivery tube is used to deliver the filter 10 over the guidewire 12 to a desired position within a body vessel whereupon the filter is ejected from the delivery tube. Now the previously collapsed stent 14 expands into contact with the walls 36 of the vessel (shown in broken lines) thereby expanding the flexible mesh filter material which was previously collapsed within the delivery tube with the stent. The guidewire 12 may now be used to guide other devices into the vessel, and since the guidewire can move freely in a longitudinal direction within the tube 11, longitudinal movement of the guidewire will not result in movement of the expanded filter.

Once the stent 14 has expanded against the wall 36 of the vessel, the guidewire 12 can be removed and replaced with a new guidewire of a different size. The tube 11 is preferably formed with an internal dimension of sufficient size to accept 0.014 inch diameter to 0.035 inch diameter guidewires. It may often be desirable to initially use a very fine guidewire (0.014") to cross a lesion and position the filter 10 and to then exchange this fine guidewire for a thicker wire. The details of the association of the guidewire with the tube 11 will be set forth in detail hereinbelow.

The fine mesh filter material 22, when expanded, should have a pore size within a range of 100 Mm to 150 Mm to capture and retain embolic material sized in excess of the pore size while permitting blood flow in the direction of the arrow 38 line in FIG. 1 between the wires 16 and into the proximal end 18 of the stent 14. The blood and embolic material flows through the and into the flexible conical section 26 of the fine mesh filter material where the embolic material is trapped while the blood passes through the filter material.

To remove the filter 10 with the captured embolic material, the stent 14 is collapsed against the tube 11 for withdrawal through a catheter or delivery tube 34. Preferably the stent is formed of the thermal shape memory material such as nitinol and may be collapsed by cooling the stent to a temperature below a transition temperature. It is important to note that the embolic material has been captured within the conical section 28, so that when the stent collapses against the tube 11, it positively closes the mouth of the conical section preventing material from escaping as the filter is drawn into the tube 34. The stent forces the entire longitudinal extent of the section 32 against the tube 11 to prevent the escape of material from the conical section 28.

The guidewire 12 has an elongate, flexible body 13 which extends from a distal end of the wire 15 to a proximal end 17 which projects beyond the proximal end of the catheter or delivery tube 34. Adjacent to the distal end 15 of the guidewire 12 is an expandable and contractable stop member 19 which moves between a contracted position adjacent to the guidewire and an expanded position as shown in FIG. 1. In the contracted position of the stop member, the stop member is dimensioned to move freely with the guidewire 12 through the tube 11, but once through the tube, the stop member can be manually or automatically expanded to prevent migration of the filter over the distal end of the guidewire. In the expanded position, the stop member has an outer dimension which is larger than the internal dimension of the channel through the tube 11, but the outer dimension of the expanded stop member is radially spaced from the inner wall 36 of the blood vessel. This is important as contact by the stop member with the vessel wall would dislodge plaque downstream of the filter 10 as the guidewire moves during an intervascular procedure.

With the stop member 19 in the expanded position, the guidewire 12 can still move longitudinally relative to the filter 10, but may not be withdrawn from the filter nor may the filter migrate over the distal end of the guidewire. A number of stop member structures will subsequently be discussed, but the stop member could be formed of two or more short arms 21 and 23 secured at one end to the guidewire 12. These arms can be constructed of spring metal or of nitinol so that they lie flat against the guidewire as it passes through the catheter 34 and spring outwardly as the guidewire and filter leave the catheter.

Figure 2:
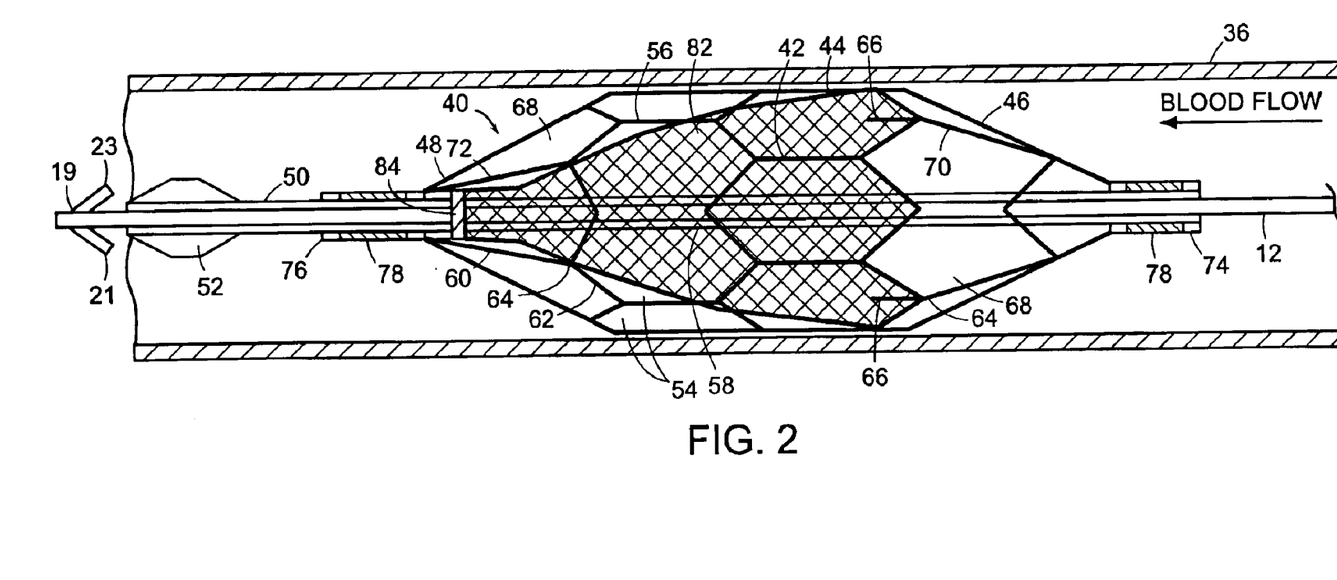
FIG. 2 is a partially sectional view in side elevation of a second free standing filter which can readily accommodate the guidewire of the present invention.
Figure 3:
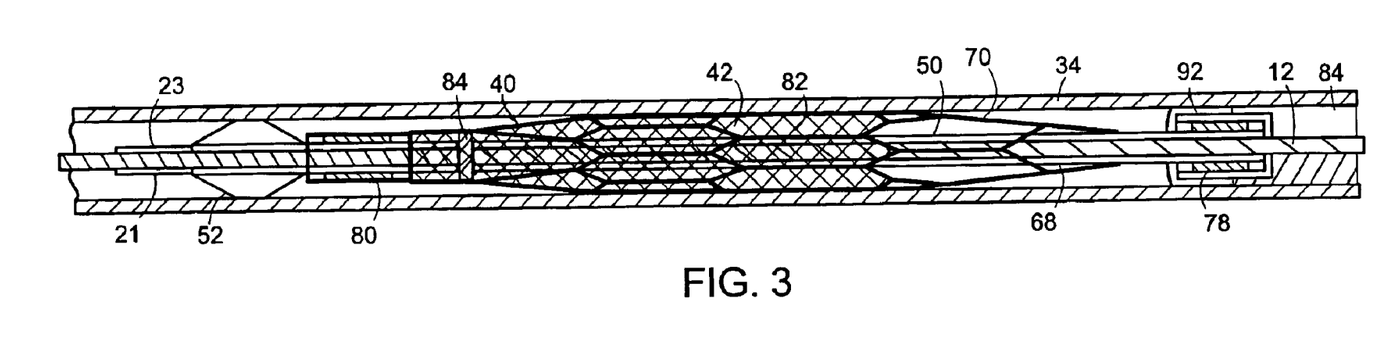
FIG. 3 is a partially sectional view of the free standing filter of FIG. 2 within a delivery tube having the guidewire in accordance with the present invention positioned therein with the stop member retracted.

Referring now to FIGS. 2 and 3, a second example of a free standing filter which may readily accommodate the guidewire 12 in accordance with the present invention is indicated generally at 40. For unimpeded passage through a catheter or delivery tube 34, it is beneficial to form a filter with a frame which completely surrounds and protects the filter mesh material. Thus the filter 40 includes a cellular frame 42 which is preferably formed of thermal shape memory material such as nitinol, and this frame when expanded includes a central section 44 having a substantially tubular configuration, a proximal end section 46 and a distal end section 48, both having a substantially conical configuration. A central tube 50, similar in size and structure to the tube 11, forms the central longitudinal axis for the filter 40 and extends through the filter and outwardly from the proximal and distal sections of the frame 42. The distal end of the tube 50 is provided with a tapered a traumatic molded tip 52 configured to center and guide the filter within the delivery tube 34.

The central section 44 of the frame 42 includes a plurality of interconnected cells 54 which are substantially equal in size and which are defined by spaced sidewalls 56 and 58 which extend substantially parallel to the tube 50 and the longitudinal axis of the filter. Adjacent cells 54 in a row of cells extending around the central tube 50 are connected together by their adjacent sidewalls 56 and 58, and these sidewalls remain substantially parallel to the tube 50 in both the expanded and collapsed configuration of the filter 40 as illustrated in FIGS. 2 and 3. The opposite ends of each cell are formed by outwardly inclined endwall sections 60 and 62 which meet at an apex 64. Extending in a distal direction from the apex 64 of alternate cells 54 at the proximal end of the central section 44 are short, straight stabilizers 66 which engage the vessel wall 36 when the filter is expanded and aid to preclude movement of the filter in a distal direction.

The proximal end section 46 and distal end section 48 of the frame 42 are formed of cells 68 with tapered sidewalls 70 and 72 which extend at an angle to the central tube 50 to form the tapered conical end sections of the frame. Proximal end section 46 of the frame is secured to the tube 50 by a coupling 74, and distal end section 48 is secured to a coupling 76 which slides on the tube 50. The couplings 74 and 76 are provided with radiopaque markers 78 and 80 respectively.

Fine mesh filter material 82 of the type previously described for the filter 10 is positioned within the central and distal sections of the frame 42. This filter material is bonded to at least the first row of cells 54 in the proximal end of the central section 44 of the frame, and at the distal end of the frame the filter material is secured to the tube 50 adjacent to the coupling 76 by a coupling 84. Thus the filter material forms a cone when the filter 40 is expanded, and the open proximal end of the cone is positively closed when the proximal end row of cells of the central section 44 collapse against the tube 50.

As shown in FIG. 3, when the filter 40 moves along the guidewire 12 through the delivery tube 34, the mesh filter material 82 is enclosed within the frame 42 which protects the filter material. Also, when an expanded filter is contracted and drawn back into the delivery tube, the frame engages the delivery tube and precludes the filter from catching or snagging on the delivery tube.

Figure 4:
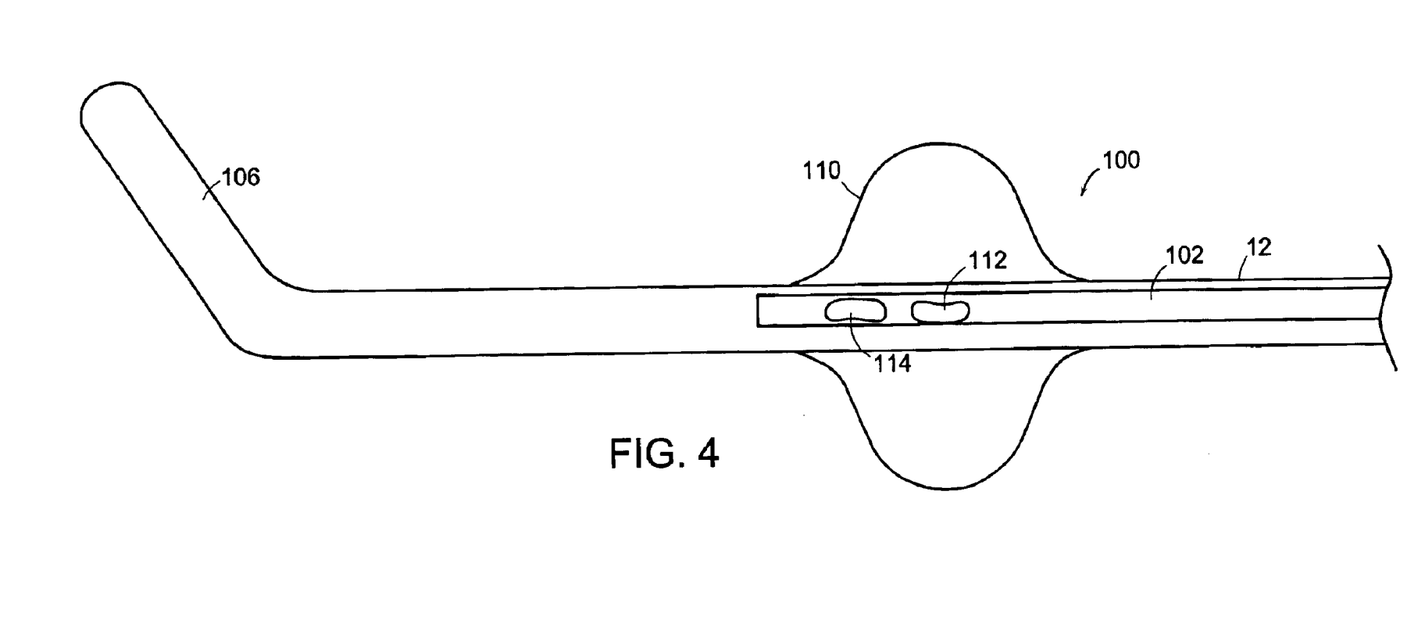
FIG. 4 is an expanded sectional view of a distal end of a guidewire in accordance with the present invention including a stop mechanism in the form of a balloon therein in an expanded condition.
Figure 5:
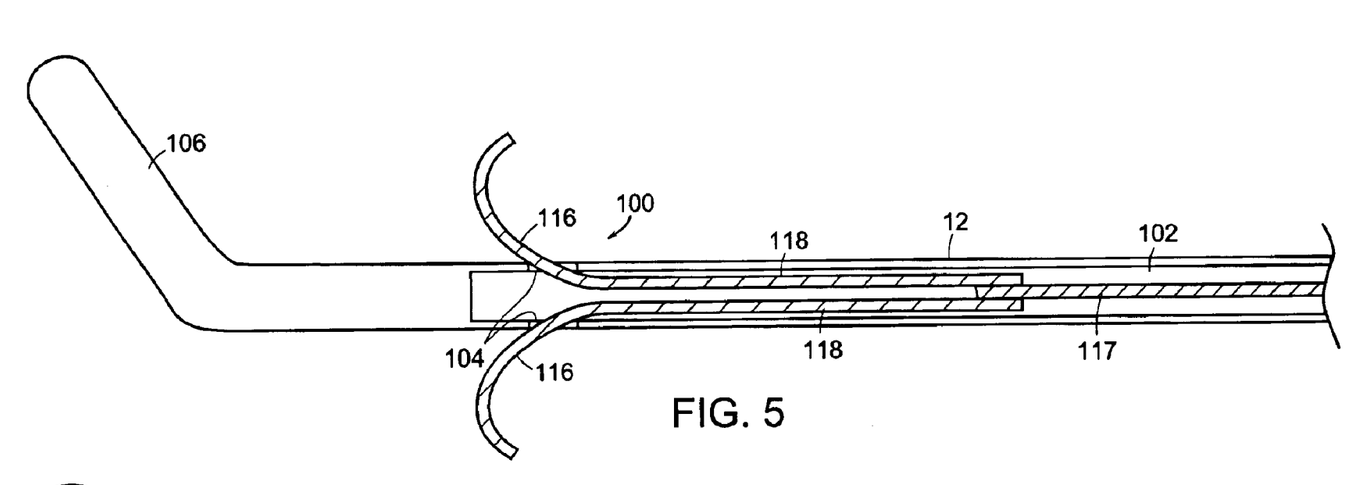
FIG. 5 is an expanded sectional view of a distal end of a guidewire in accordance with an alternative embodiment of the present invention including a stop mechanism in the form of a grapple hook in an extended position.

With reference now to FIG. 4, an initial embodiment of the guidewire set forth in accordance with the present invention is illustrated therein. FIG. 4 illustrates a distal end of the guidewire 12 which includes the stop mechanism 100 in the form of an elastic balloon mounted around the guidewire which is expandable and collapsible with respect to the guidewire 12. The guidewire defines an enclosed, central chamber 102 which extends from the proximal end of the guidewire to the stop mechanism 100 and through which air can be provided to expand the balloon. The balloon 110 is expandable and collapsible with respect to the guidewire 12 by way of ports 112 and 114 which connect the interior of the balloon to the channel 102. As can be appreciated by one of ordinary skill in the art, when the balloon 110 of the guidewire 12 is expanded to a condition illustrated in FIG. 4, a filter or other free standing intervascular device, if dislodged from a vessel during an angioplasty or other procedure, would be stopped by the stop mechanism 100 in that the balloon is expandable to a dimension greater than that of the tube 11 of the filter or device but to a dimension which is less than the fully expanded dimension of the intervascular device. Accordingly, the operation can confidently take place knowing that the filter or device will not become lost within the vessel. Further, in order to permit the exchange of guidewires as referred to hereinabove, the balloon is selectably collapsible so as to allow the guidewire 12 to be intentionally removed from the tube 11 in order to allow for exchange of guidewires.

With reference to FIGS. 5, 6, 7 and 8, various embodiments of the present invention are set forth. As noted from FIG. 5, extendable and retractable grappling hooks 116 are mounted to slide within the channel 102 and are provided to form a positive stop which is extendable from the guidewire 12 for a sufficient radius so as to ensure that the tube 11 of the filter cannot pass thereby. The grappling hooks 116 may be extendable from the guidewire 12 in any known manner. For example, a flexible rod 117 slidable within the channel 102 and connected to the hook extensions 118 can move axially with respect to the guidewire 12 and permit the extension and retraction of the grappling hooks 116.

The grappling hooks 116 may be extended and retracted through openings 104 formed on opposite sides of the guidewire which open into the channel 102. The grappling hooks may be formed of spring metal strips which curl outwardly when the hooks are extended or may be formed of strips of thermal shape memory material such as nitinol having a temperature transition level such that the hooks curl to the configuration shown in FIG. 5 when they are extended from the guidewire within a blood vessel. Again, the extended configuration of the hooks is such that they cannot pass through the tube 11, but when fully extended, they do not extend to the extent of the extended position of the intervascular device through which the guidewire passes.

Figure 6:
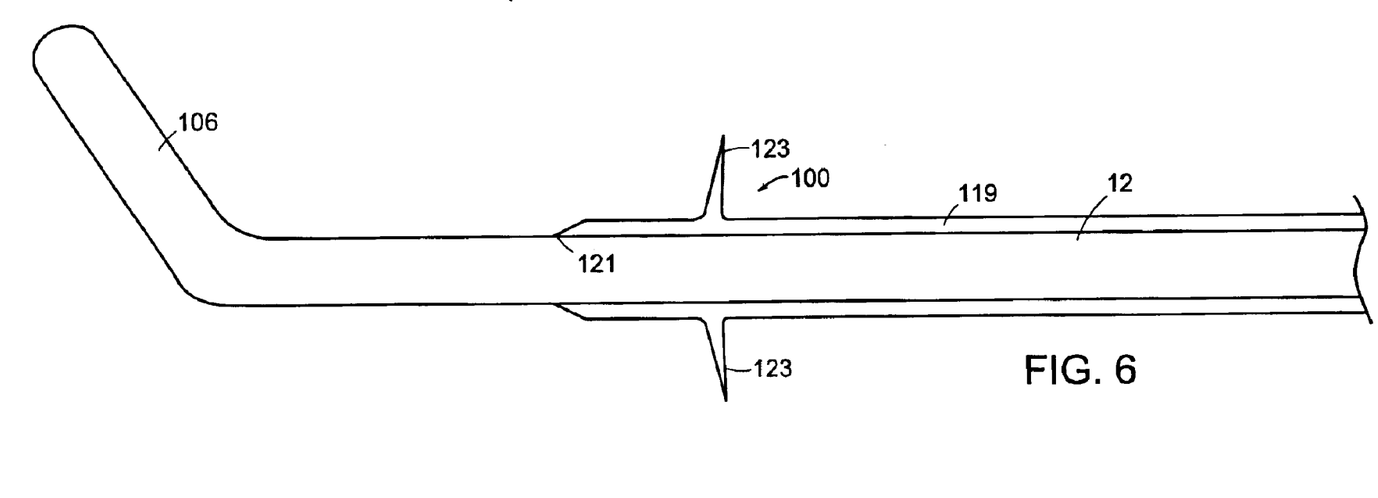
FIG. 6 is an expanded sectional view of a distal end of a guidewire in accordance with an alternative embodiment of the present invention including a stop mechanism in the form of a buckled tube in an expanded condition.

Alternatively, as illustrated in FIG. 6, the stop mechanism 100 may take the configuration of a buckle tube 119 which is slidably mounted on the guidewire 12 but is attached to the guidewire at its distal end 121. When the tube 119 is displaced relative to the guidewire toward the distal end 106 of the guidewire, the wall of the tube will buckle outwardly thus forming a circumferential extension 123. As with the grappling hooks 116, this circumferential extension extends radially for a distance greater than a diameter of the tube 11 but less than the expanded position of the filter or other intervascular device through which the guidewire passes. Accordingly, the filter would be prevented from traveling beyond the end of the guidewire 12 when the stop mechanism 100 is in the expanded condition. The buckle tube has a thin, flexible wall which reengages the guidewire when the buckle tube is moved axially toward the proximal end of the guidewire.

Figure 7:
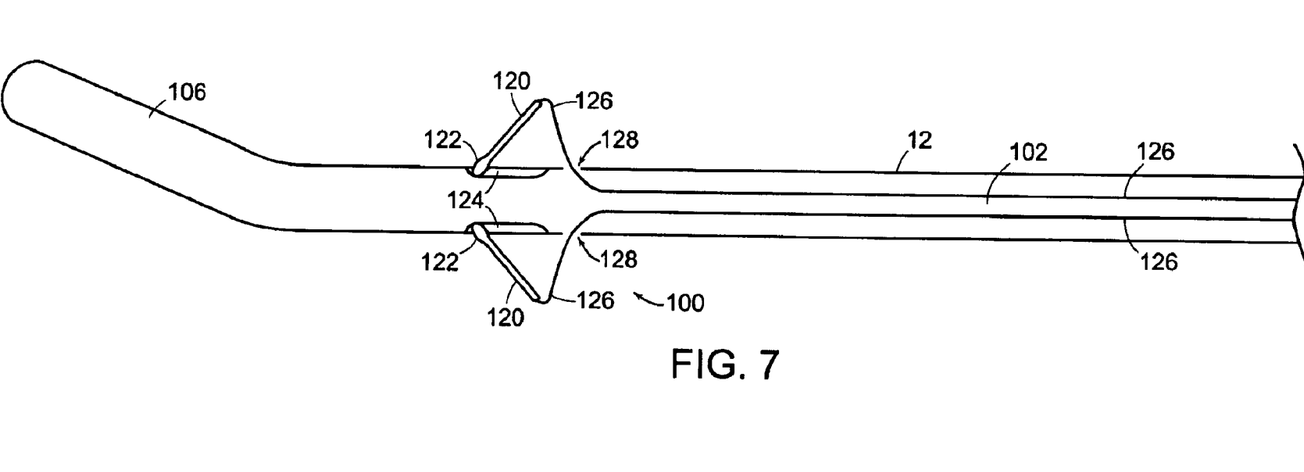
FIG. 7 is an expanded sectional view of a distal end of a guidewire in accordance with an alternative embodiment of the present invention including a stop mechanism in the form of barbs in an extended position.

In accordance with yet another embodiment of the present invention, the stop mechanism 100 may take on the form of barbs 120 which are extendable and retractable with respect to the guidewire 12. Again a mechanism which is moved axially with respect to the guidewire 12 may be utilized in order to extend and retract the barbs 120 with respect to the guidewire 12. The barbs 120 when extended would be of a dimension greater than that of the tube 11 of the filter or intervascular device and when retracted would be permitted to readily pass through the tube 11.

The barbs 120 may be formed of spring metal with each having an end secured at 122 to the guidewire 12. These barbs, when retracted, lie within depressions 124 formed in the exterior surface of the guidewire, and when released, the spring bias of the barbs causes them to extend outwardly as shown in FIG. 7. An elongate, flexible tether 126 is connected to the free end of each of the barbs 120 and passes through a hole 128 into the channel 102 in the guidewire 12. When the tethers 126 are drawn toward the proximal end of the guidewire, the barbs 120 are retracted into the depressions 124.

Figure 8:
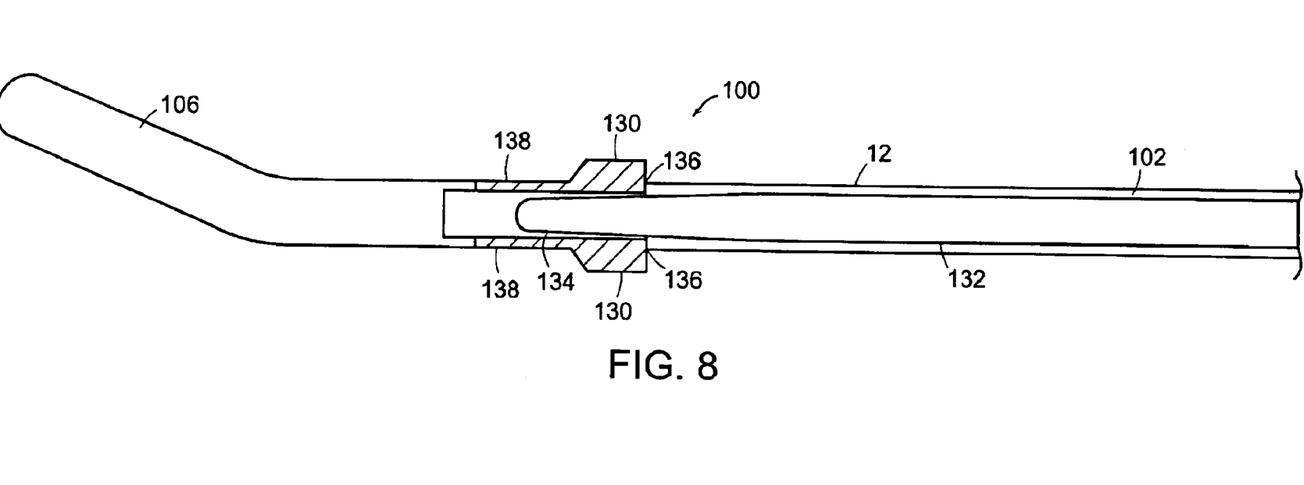
FIG. 8 is an expanded view of a distal end of a guidewire in accordance with an alternative embodiment of the present invention including a stop mechanism in the form of a boss element in an extended position.

In FIG. 8, the stop mechanism 100 takes the form of double boss elements 130 which are spring biased with respect to the guidewire 12 and pressed outwardly by an elongate cam actuator 132 which extends axially through the channel 102 in the guidewire 12. The actuator 132 includes a chamfered cam surface 134 which cooperates with the boss elements 130 to extend such elements outwardly with respect to the guidewire 12. Again the outward extension of the boss elements would be of a dimension greater than that of the tube 11 of the filter thus preventing passage of the filter beyond the end of the guidewire 12 when the boss elements are extended.

Each boss element extends through an opening 136 in the guidewire and is attached to a mounting arm 138 secured within the channel 102. The mounting arms 138 spring bias the bosses 130 into the channel 120, but when the actuator 132 is moved toward the distal end 106 of the guidewire, the cam surface 134 forces the bosses outwardly against the spring bias through the openings 136.

I claim:

1. A medical apparatus comprising:
   an intervascular device comprising a contracted configuration and an expanded configuration, said intervascular device comprising an elongate wire receiving unit having an open ended channel extending therethrough for receiving a guidewire; and
   said guidewire comprising an elongate body extending along a longitudinal axis between a proximal end and a distal end and an expandable and contactable stop member mounted thereon which is movable between a first contracted position and a second expanded position, said expandable and contactable stop member being dimensioned to pass through said channel in the first contracted position and being dimensioned in the second expanded position thereof to have an outer dimension which is greater than the inner dimension of said channel but less than the outer dimension of said intervascular device in the expanded configuration thereof, and said elongate body comprising an outer dimension which is less than the inner dimension of said channel to permit free movement of said guidewire relative to said intervascular device within said channel in opposite directions along the longitudinal axis of said guidewire.

2. The apparatus of claim 1 wherein said expandable and contractable stop member is spaced from both the proximal and distal ends of said guidewire body.

3. The apparatus of claim 1 wherein said expandable and contractable stop member comprises a thin walled body member mounted upon and surrounding said guidewire and dimensioned to pass with said guidewire through said channel in the first contracted position of said contactable stop member, said thin walled body member comprising a body member distal end portion secured to said guidewire and a sliding portion extending toward the proximal end of said guidewire, said sliding portion being longitudinally slidable relative to said guidewire toward the distal end of said guidewire to cause the thin walled body member to bow outwardly from said guidewire adjacent to the body member distal end portion to form the second expanded position of said expandable and contractable stop member.

4. The apparatus of claim 1 wherein said guidewire is formed with an internal chamber extending from the proximal end of said guidewire toward said distal end thereof, and a stop member operating mechanism is mounted in said internal chamber to move said expandable and contractable stop member between said first contracted and second expanded positions.

5. The apparatus of claim 4 wherein said guidewire body comprises at least one opening formed to extend into said internal chamber, said expandable and contractable stop member comprising at least one stop unit retractable through said opening into said internal chamber to the first contractable position of said expandable and contractable stop member and extendable outwardly through said opening to the second expanded position of said expandable and contractable stop member.

6. The apparatus of claim 5 wherein said at least one stop unit comprises a boss element which extends through said opening and a mounting arm secured within said internal channel to said boss element and to said guidewire body.

7. The apparatus of claim 6 wherein said stop member operating mechanism comprises an elongate cam actuator movable within the integral chamber to engage said stop unit and force said boss element to move outwardly through the opening in said guidewire body to the second expanded position of said expandable and contractable stop member.

8. The apparatus of claim 7 wherein said mounting arm is formed to bias said boss unit into said internal chamber.

9. The apparatus of claim 7 wherein said guidewire body comprises tow opposed openings into said internal chamber, and said expandable and contractable stop member comprises a boss element extending through each said opening, each said boss element being secured within internal chamber to a separate mounting arm secured to said guidewire within said internal chamber.

10. The apparatus of claim 9 wherein said elongate cam actuator is movable between said boss elements to engage and force said boss elements outwardly through said openings.

11. The apparatus of claim 10 wherein the mounting arm for each boss element is formed to bias boss element into said internal chamber.

12. The apparatus of claim 5 wherein said expandable and contractable stop member comprises at least one elongate strip of material which engages said stop member operating mechanism within said internal chamber and is extendable thereby through said at least one opening in said guidewire.

13. The apparatus of claim 12 wherein said strip of material is spring metal.

14. The apparatus of claim 12 wherein said strip of material is formed of temperature responsive shape memory material.

15. The apparatus of claim 4 wherein said expandable and retractable stop member comprises at least one barb having a first end secured externally to said guidewire body, said barb being formed normally extend from said first end angularly outward from said guidewire to a second end of said barb, said guidewire body comprising at least one opening formed to extend into said internal chamber, and said stop member operating mechanism comprising an elongate tether connected to the second free end of said barb and extending through said opening into said internal chamber.

16. The apparatus of claim 15 wherein said barb is formed of flexible material which biases said barb angularly outward from said guidewire body, said tether operating to draw the second end of said barb against the bias toward said guidewire body.

17. The apparatus of claim 1 wherein said guidewire body is formed with an internal chamber extending from the proximal end of the guidewire body toward the distal end thereof, said expandable and contractable stop member comprising an inflatable unit secured externally to said guidewire body, said guidewire body comprising at least one opening connecting said internal chamber to said inflatable unit.

18. An elongate guidewire for use with a free, unsecured intervascular device comprising an expanded configuration for contact with the inner wall of a blood vessel and an elongate, enclosed, open ended channel comprising a channel inner dimension for receiving said guidewire, said guidewire comprising:

an elongate, flexible body extending along a longitudinal axis between a proximal end and a distal end, said flexible body comprising and outer dimension which is less than the inner dimension of said channel to permit free movement of said guidewire relative to said intervascular device within said channel along the longitudinal axis of said guidewire, and an expandable and contractable stop member mounted on said guidewire body for movement between a first contracted position and a second expanded position, said expandable and contractable stop member being dimensioned in the first contracted position to move through said channel and being dimensioned in the second expanded position thereof to comprise an outer dimension which is greater than the inner dimension of said channel but less than an outer dimension of said intervascular device in the expanded configuration thereof.

19. The guidewire of claim 18 wherein said expandable and contractable stop member comprises a thin walled body member mounted upon and surrounding said guidewire and dimensioned to pass with said guidewire through said channel in the first contracted position of said contractable stop member, said thin wall body member comprising a body member distal end portion secured to said guidewire and a sliding portion extending toward the proximal end of said guidewire, said sliding portion being longitudinally slidable relative to said guidewire toward the distal end of said guidewire to cause the thin walled body member to bow outwardly from said guidewire adjacent to the body member distal end portion to form the second expanded position of said expandable and contractable stop member.

20. The guidewire of claim 18 wherein said guidewire is formed with an internal chamber extending from the proximal end of said guidewire toward said distal end thereof, and stop member operating mechanism is mounted in said internal chamber to move said expandable and contractable stop member between said first contracted and second expanded position.

21. The guidewire of claim 20 wherein said guidewire body comprises at least one opening formed to extend into said internal chamber, said expandable and contractable stop member comprising at least one stop unit retractable through said opening into said internal chamber to the first contractable position of said expandable and contractable stop member and extendable outwardly through said opening to the second expanded position of said expandable and contractable stop member.

22. The guidewire of claim 21 wherein said at least one stop unit comprises a boss element which extends through said opening and a mounting arm secured within said internal channel to said boss element to said guidewire body.

23. The guidewire of claim 22 wherein said stop member operating mechanism comprises an elongate cam actuator movable within the internal chamber to engage said stop unit and force said boss element to move outwardly through the opening in said guidewire body to the second expanded position of said expandable and contractable stop member.

24. The guidewire of claim 24 wherein said mounting arm is formed to bias said boss unit into said internal chamber.

25. The guidewire of claim 21 wherein said expandable and contractable stop member comprises at least on elongate strip of material which engages said stop member operating mechanism within said internal chamber and is extendable thereby through said at least one opening in said guidewire.

26. The guidewire of claim 20 wherein said expandable and retractable stop member comprises at least one barb having a first end secured externally to said guidewire body, said barb being formed to normally extend from said first end angularly outward from said guidewire to a second end of said barb, said guidewire body comprising at least one opening formed to extend into said internal chamber, and said stop member operating mechanism comprising an elongate tether connected to the second free end of said barb and extending through said opening into said internal chamber.

27. The guidewire of claim 26 wherein said barb is formed of flexible material which biases said barb angularly outward from said guidewire body, said tether operating to draw the second end of said barb against the bias toward said guidewire body.

28. The apparatus of claim 5 wherein said stop member comprises at least one grappling hook.

29. The guidewire of claim 18 wherein said stop member comprises at least one grappling hook.

30. A guidewire for introducing an intervascular device in a patient's body, comprising:

an elongate body along a longitudinal axis between a proximal end and a distal end; and an expandable and contractable stop member mounted thereon which is movable between a first contracted position and a second expanded position, said expandable and contractable stop member being dimensioned to pass through a channel in said intervascualr device in the first contracted position and being dimensioned in the second expanded position to comprise an outer dimension of said intervasuclar device in an expanded configuration thereof, and said elongate body comprising an outer dimension which is less than inner dimension of said channel to permit free movement of said guidewire relative to said intervascular device within said channel in opposite directions along the longitudinal axis of said guidewire.

31. The guidewire of claim 30 wherein said expandable and contractable stop member is spaced from both the proximal and distal ends of said guidewire body.

32. The guidewire of claim 30 wherein said expandable and contractable stop member comprises a thin walled body member mounted upon and surrounding said guidewire and dimensioned to pass with said guidewire through said channel in the first contracted position of said contractable stop member, said thin walled body member comprising a body member distal end portion secured to said guidewire and a sliding portion extending toward the proximal end of said guidewire, said sliding portion being longitudinally slidable relative to said guidewire toward the distal end of said guidewire to cause the thin walled body member to bow outwardly from said guidewire adjacent to the body member distal end portion to form the second expanded position of said expandable and contractable stop member.

33. The guidewire of claim 30 wherein said guidewire is formed with an internal chamber extending from the proximal end of said guidewire toward said distal end thereof, and a stop member operating mechanism is mounted in said internal chamber to move said expandable and contractable stop member between said first contracted and second expanded positions.

34. The guidewire of claim 33 wherein said expandable and retractable stop member comprises at least one barb having a first end secured externally to said guidewire body, said barb being formed to normally extend from said first end angularly outward from said guidewire to a second end of said barb, said guidewire body comprising at least one opening formed to extend into said internal chamber, and said stop member operating mechanism comprising an elongate tether connected to the second free end of said barb and extending through said operating into said internal chamber.

35. The guidewire of claim 34 wherein said barb is formed of flexible material which biases said barb angularly outward from said guidewire body, said tether operating to draw the second end of said barb against the bias toward said guidewire body.

36. The guidewire of claim 33 wherein said guidewire body comprises at least one opening formed to extend into said internal chamber, said expandable and contractable stop member comprising at least one stop unit retractable through said opening into said internal chamber to the first contractable position of said expandable and contractable stop member and extendable outwardly through said opening to the second expanded position of said expandable and contractable stop member.

37. The guidewire of claim 36 wherein said expandable and contractable stop member comprises at least one elongate strip of material which engages said stop member operating mechanism within said internal chamber and is extendable thereby through said at least one opening in said guidewire.

38. The guidewire of claim 37 wherein said strip of material is spring metal.

39. The guidewire of claim 37 wherein said strip of material is formed of temperature responsive shape memory material.

40. The guidewire of claim 36 wherein said at least one stop unit comprises a boss element which extends through said opening and a mounting arm secured within said internal channel to said boss element and to said guidewire body.

41. The guidewire of claim 40 wherein said stop member operating mechanism comprises an elongate cam actuator movable with the internal chamber to engage said stop unit and force said boss element to move outwardly through the opening in said guidewire body to the second expanded position of said expandable and contractable stop member.

42. The guidewire of claim 41 wherein said guidewire body comprises two opposed openings into said internal chamber, and said expandable and contractable stop member comprises a boss element extending through each said opening, each said boss element being secured within said internal chamber to a separate mounting arm secured to said guidewire within said internal chamber.

43. The guidewire of claim 42 wherein said elongate cam actuator is movable between said boss elements to engage and force said boss elements outwardly through said openings.

44. The guidewire of claim 43 wherein the mounting arm for each boss element is formed to bias boss element into said internal chamber.

45. The guidewire of claim 41 wherein said mounting arm is formed to bias said boss unit into said internal chamber.

46. The guidewire of claim 30 wherein said guidewire body is formed with an internal chamber extending from the proximal end of the guidewire body toward the distal end thereof, said expandable and contactable stop member comprising an inflatable unit secured externally to said guidewire body, said guidewire body comprising at least one opening connecting said internal chamber to said inflatable unit.

47. The guidewire of claim 30 wherein said stop member comprises at least one grappling hook.

\* \* \* \* \*

UNITED STATES PATENT AND TRADEMARK OFFICE
CERTIFICATE OF CORRECTION

PATENT NO. : 6,939,361 B1
DATED : September 6, 2005
INVENTOR(S) : Kleshinski et al.

It is certified that error appears in the above-identified patent and that said Letters Patent is hereby corrected as shown below:

Column 10,
Line 20, replace "tow" with -- two --.
Line 31, after "formed to bias" insert -- said --.
Line 46, after "barb being formed" insert -- to --.

Column 11,
Line 28, replace "wall" with -- walled --.
Line 43, replace "position" with -- positions --.
Line 63, replace "claim 24" with -- claim 23 --.

Column 12,
Line 30, replace "intravasculr" with -- intravascular --.
Line 33, between "dimension" and "of said channel" insert -- which is greater than the inner dimension of said channel but less than an outer dimension --.

Column 14,
Line 20, after "formed to bias" insert -- said --.

Signed and Sealed this

Twenty-fifth Day of April, 2006

JON W. DUDAS
*Director of the United States Patent and Trademark Office*